United States Patent
Schmidt et al.

(10) Patent No.: US 8,729,469 B1
(45) Date of Patent: May 20, 2014

(54) MULTIPLE SAMPLE ATTACHMENT TO NANO MANIPULATOR FOR HIGH THROUGHPUT SAMPLE PREPARATION

(71) Applicant: FEI Company, Hillsboro, OR (US)

(72) Inventors: Michael Schmidt, Gresham, OR (US);
Stacey Stone, Beaverton, OR (US);
Corey Senowitz, San Diego, CA (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/935,720

(22) Filed: Jul. 5, 2013

Related U.S. Application Data

(60) Provisional application No. 61/794,816, filed on Mar. 15, 2013.

(51) Int. Cl.
*H01J 37/20* (2006.01)
(52) U.S. Cl.
CPC ..................................... *H01J 37/20* (2013.01)
USPC ....................... 250/309; 250/492.21; 250/311

(58) Field of Classification Search
USPC ..................... 250/309, 492.21, 311
See application file for complete search history.

(56) References Cited

U.S. PATENT DOCUMENTS

| | | | |
|---|---|---|---|
| 7,791,050 B2* | 9/2010 | Tomimatsu et al. | 250/492.21 |
| 8,134,124 B2 | 3/2012 | Blackwood et al. | |
| 8,357,913 B2 | 1/2013 | Agorio et al. | |
| 8,525,137 B2 | 9/2013 | Blackwood et al. | |
| 8,536,525 B2 | 9/2013 | Blackwood et al. | |
| 2013/0153785 A1 | 6/2013 | Agorio et al. | |

* cited by examiner

*Primary Examiner* — Kiet T Nguyen
(74) *Attorney, Agent, or Firm* — Scheinberg & Associates, PC; Michael O. Scheinberg; Ki O

(57) ABSTRACT

An improved method for extracting and handling multiple samples for S/TEM analysis is disclosed. Preferred embodiments of the present invention make use of a micromanipulator that attaches multiple samples at one time in a stacked formation and a method of placing each of the samples onto a TEM grid. By using a method that allows for the processing of multiple samples, the throughput of sample prep in increased significantly.

17 Claims, 11 Drawing Sheets

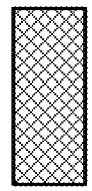
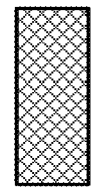
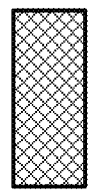
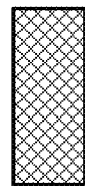
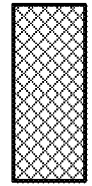
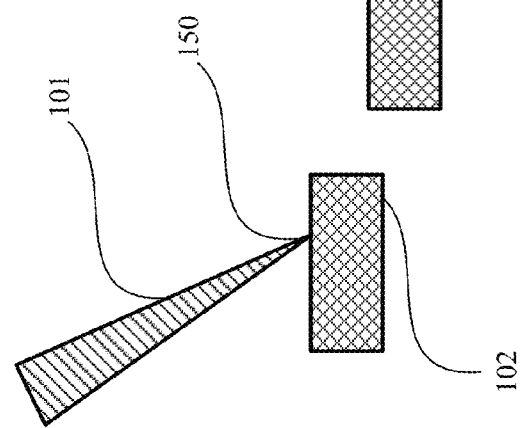
FIG. 3
FIG. 4

MULTIPLE SAMPLE ATTACHMENT TO NANO MANIPULATOR FOR HIGH THROUGHPUT SAMPLE PREPARATION

This application claims priority from U.S. Prov. Appl. No. 61/794,816, filed Mar. 15, 2013 which is hereby incorporated by reference.

TECHNICAL FIELD OF THE INVENTION

The present invention relates to the extraction and handling of samples for transmission electron microscopes and scanning transmission electron microscopes.

BACKGROUND OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or an electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting lines, spacing and diameter of contact holes, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

Typically, CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

Transmission electron microscopes (TEMs) allow observers to see extremely small features, on the order of nanometers. In contrast SEMs, which only image the surface of a material, TEM also allows analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site. Samples, also referred to as lamellae, are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

Because a sample must be very thin for viewing with transmission electron microscopy (whether TEM or STEM), preparation of the sample can be delicate, time-consuming work. The term "TEM" as used herein refers to a TEM or an STEM and references to preparing a sample for a TEM are to be understood to also include preparing a sample for viewing on an STEM. The term "S/TEM" as used herein also refers to both TEM and STEM.

Several techniques are known for preparing TEM specimens. These techniques may involve cleaving, chemical polishing, mechanical polishing, or broad beam low energy ion milling, or combining one or more of the above. The disadvantage to these techniques is that they are not site-specific and often require that the starting material be sectioned into smaller and smaller pieces, thereby destroying much of the original sample.

Other techniques generally referred to as "lift-out" techniques use focused ion beams to cut the sample from a substrate or bulk sample without destroying or damaging surrounding parts of the substrate. Such techniques are useful in analyzing the results of processes used in the fabrication of integrated circuits, as well as materials general to the physical or biological sciences. These techniques can be used to analyze samples in any orientation (e.g., either in cross-section or in plan view). Some techniques extract a sample sufficiently thin for use directly in a TEM; other techniques extract a "chunk" or large sample that requires additional thinning before observation. In addition, these "lift-out" specimens may also be directly analyzed by other analytical tools, other than TEM. Techniques where the sample is extracted from the substrate within the FIB system vacuum chamber are commonly referred to as "in-situ" techniques; sample removal outside the vacuum chamber (as when the entire wafer is transferred to another tool for sample removal) are call "ex-situ" techniques.

Samples which are sufficiently thinned prior to extraction are often transferred to and mounted on a metallic grid covered with a thin electron transparent film for viewing. FIG. 1 shows a sample mounted onto a prior art TEM grid 10. A typical TEM grid 10 is made of copper, nickel, or gold. Although dimensions can vary, a typical grid might have, for example, a diameter of 3.05 mm and have a middle portion 12 consisting of cells 14 of size 90×90 µm² and bars 13 with a width of 35 µm. The electrons in an impinging electron beam will be able to pass through the cells 14, but will be blocked by the bars 13. The middle portion 12 is surrounded by an edge portion 16. The width of the edge portion is 0.225 mm. The edge portion 16 has no cells, with the exception of the orientation mark 18. The thickness 15 of the thin electron transparent support film is uniform across the entire sample carrier, with a value of approximately 20 nm. TEM specimens to be analyzed are placed or mounted within cells 14.

During the extraction process, the wafer containing the completed lamella is removed from the FIB and placed under an optical microscope equipped with a micromanipulator. A probe attached to the micromanipulator is positioned over the lamella and carefully lowered to contact it. Electrostatic forces will attract lamella to the probe tip. The probe tip with attached lamella is then typically moved to a TEM grid. Alternatively, the attachment of the lamella to the probe tip can be done using FIB deposition.

Samples which require additional thinning before observation are typically mounted directly to a TEM sample holder. FIG. 2 shows a typical TEM sample holder 31, which comprises a partly circular 3 mm ring. In some applications, a sample 30 is attached to a finger 32 of the TEM sample holder by ion beam deposition or an adhesive. The sample extends from the finger 32 so that in a TEM (not shown) an electron beam will have a free path through the sample 31 to a detector under the sample. The TEM sample is typically mounted horizontally onto a sample holder in the TEM with the plane of the TEM sample perpendicular to the electron beam, and the sample is observed.

Unfortunately, preparation of TEM samples using such prior art methods of sample extraction are time consuming. Conventional work flow usually has a user pick up one sample at a time and placed on the TEM sample holder. First, the sample is prepped. Using a micromanipulator, the sample is lifted out. The sample is then moved to a sample holder, positioned, and then lowered so the electrostatic forces will "drop off" the sample. The sample can also be removed and placed on the location of a TEM sample holder by physically severing the connection. CD metrology often requires multiple samples from different locations on a wafer to sufficiently characterize and qualify a specific process. In some circumstances, for example, it will be desirable to analyze from 15 to 50 TEM samples from a given wafer. When so many samples must be extracted and measured, using known methods the total time to process the samples from one wafer can be days or even weeks. Even though the information that can be discovered by TEM analysis can be very valuable, the entire process of creating and measuring TEM samples has historically been so labor intensive and time consuming that it has not been practical to use this type of analysis for manufacturing process control. For the user to prep and remove each of the TEM samples, the user must perform these steps repeatedly. In other words, the user repeats the steps of prepping another sample. The user then repeats the step of lifting the sample out. Then, the user moves the sample to the TEM sample holder one at a time. This current process for high volume TM lamella prep is performed serially, and the process is often time consuming and labor intensive.

Speeding up the process of sample extraction and transfer would provide significant advantages in both time and potential revenue by allowing a semiconductor wafer to be more rapidly returned to the production line. What is needed is an improved method for TEM sample analysis, including new ways of extracting more than one sample at a time.

SUMMARY OF THE INVENTION

An object of the invention, therefore, is to provide an improved method for TEM sample analysis that increases throughput for high volume sample preparation. Preferred embodiments of the present invention provide improved methods that allows for multiple pickups and drop off of samples that allows for efficient processing of the samples. The preferred embodiment of the present invention allows for a method to stack and multiple samples to each other to move the samples to the TEM sample holder with fewer steps. This process also minimizes stage motions, gas injection system (GIS) insert/retract action and manipulator insert/retract actions.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIG. 3 shows multiple samples.

FIG. 4 shows one sample being picked up by the manipulator.

DETAILED DESCRIPTION OF PREFERRED EMBODIMENTS

Preferred embodiments of the present invention provide a method of picking up and dropping of multiple samples onto a TEM sample holder, or TEM grid, which is done to increase throughput that will involve a less labor-intensive process.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable.

In a preferred embodiment of the present invention, one or more lamellae are first created on a wafer or other substrate. FIG. 3 shows a number of lamellas 100 that have been milled or processed for preparation to be removed from the wafer. Preferably, a number of lamellas can be created using an automated ex-situ process where a lamella is thinned in place before removal as described in U.S. Provisional App. 60/853, 183 by Blackwood et al. for "Method for S/TEM Sample Analysis" (which is hereby incorporated by reference). The sample milling process can be used to create one or more lamellae at different sites on a wafer or other substrate. This method could also be used for multiple chunk type extractions to a finger type grid.

Once the desired number of lamellas has been created and prepped, a micromanipulator is used to extract the lamellas. The list of all lamella sites, including the x-y coordinates for each lamella location, for each wafer can be transferred to the extraction tool from the FIB system used to mill the lamellae. As shown in FIG. 4, the micromanipulator 101 is an electrostatic/pressure manipulator where the electrostatic forces will attract the lamella 102 to a probe tip 150. The lamella extraction process is preferably fully automated. Alternatively, the extraction process can be completely or partially controlled manually.

Figure 1:
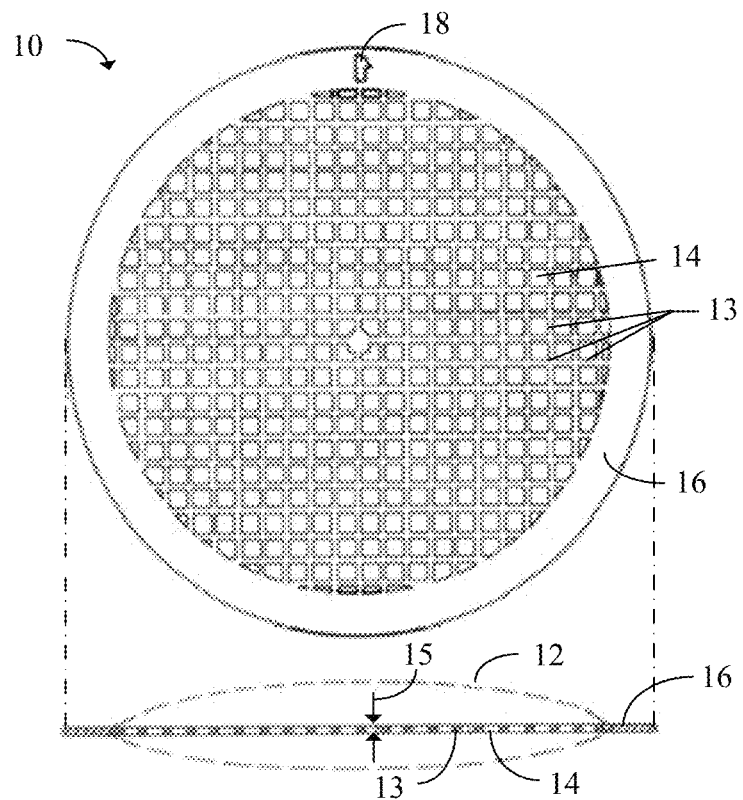
FIG. 1 shows a typical prior art TEM grid.
Figure 2:
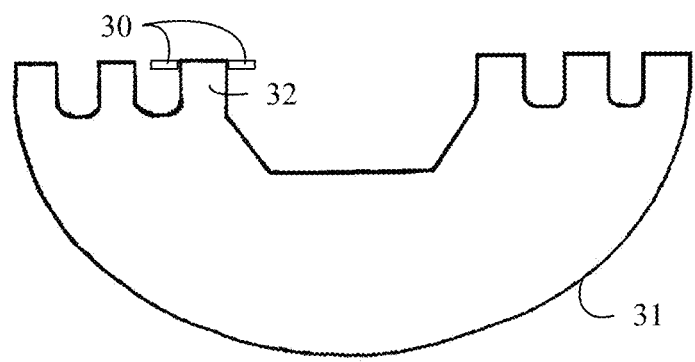
FIG. 2 shows a typical prior art TEM sample holder.
Figure 5:
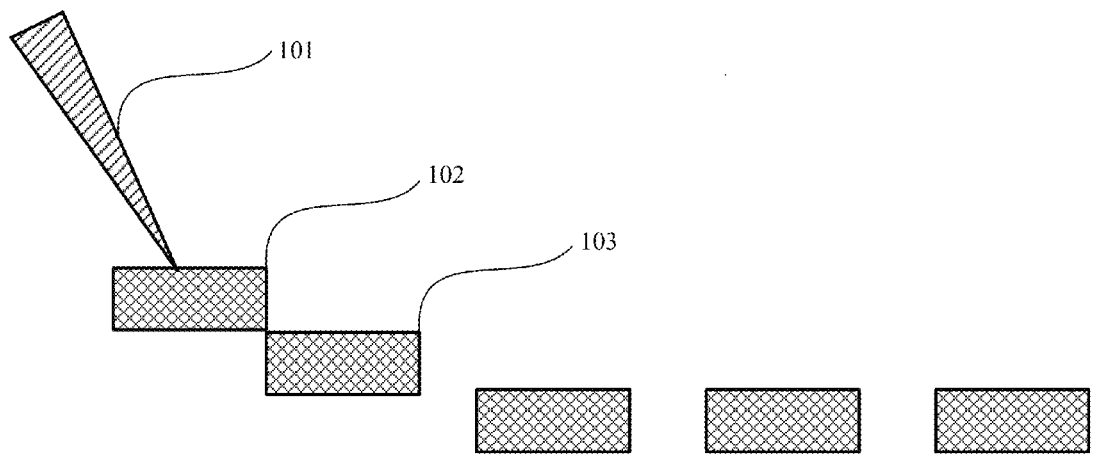
FIG. 5 shows 2 samples being picked up by the manipulator.
Figure 6:
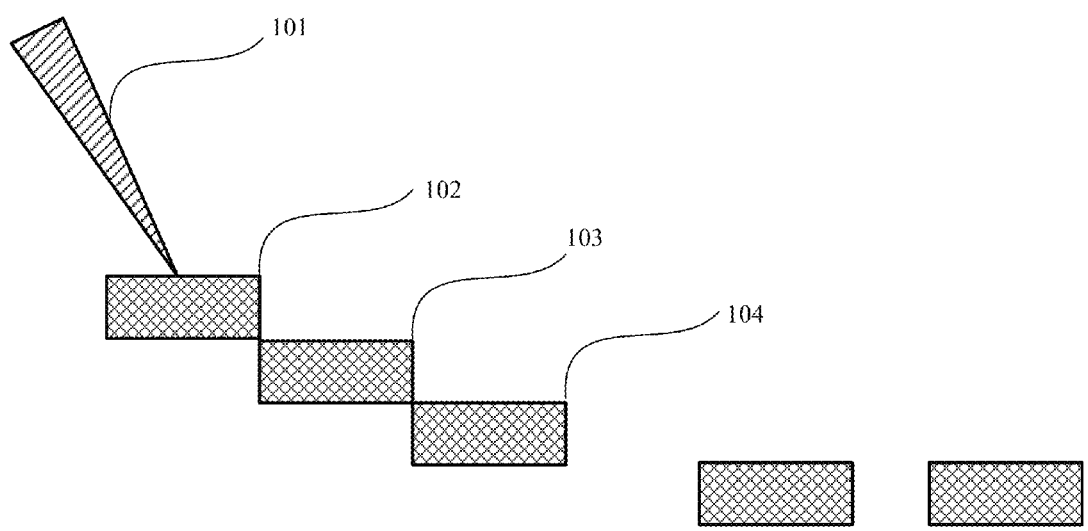
FIG. 6 shows 3 samples being picked up by the manipulator.

As shown in FIG. 5, the micromanipulator, or nano-manipulator, will then be moved to a different location containing the next lamella 103 that is ready for extraction. The micromanipulator 101 and the attached lamella 102 will be lowered so that lamella 102 is in contact with lamella 103. Electrostatic forces will attract lamella 103 to lamella 102 attaching lamella 103 to 102 to for a stack of lamella. Alternatively, the attachment of the lamella to each other can be done by welding the lamellas using FIB deposition or electron beam, friction fitting, or wherein keyed type connections could be made, which is known in the industry. As shown in FIG. 6, the process is repeated with the next lamella 104. Where the sample to be extracted has a vertical sample face, this results in the probe being also oriented at a 45 degree angle relative to the sample face.

Figure 7:
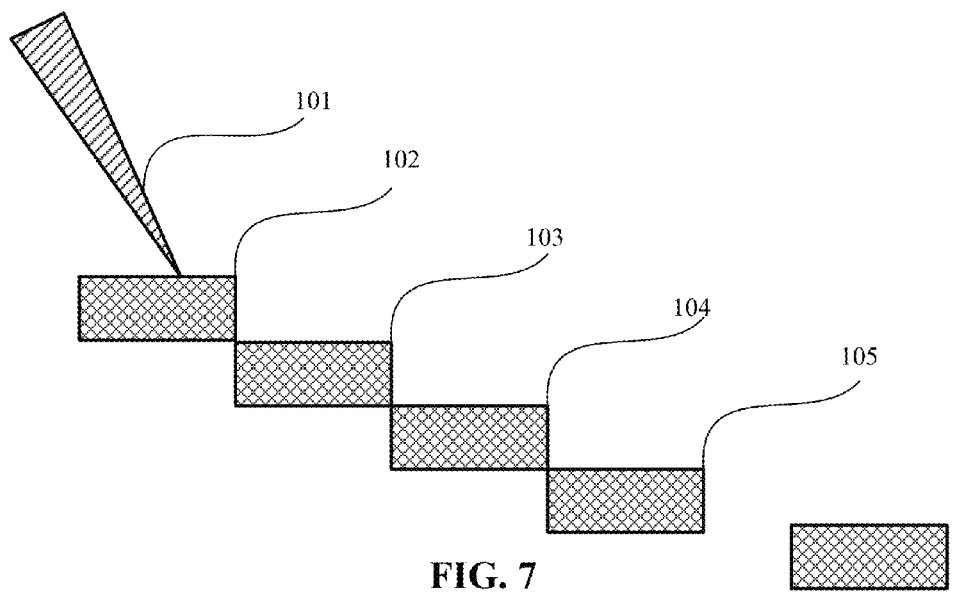
FIG. 7 shows 4 samples being picked up by the manipulator.
Figure 8:
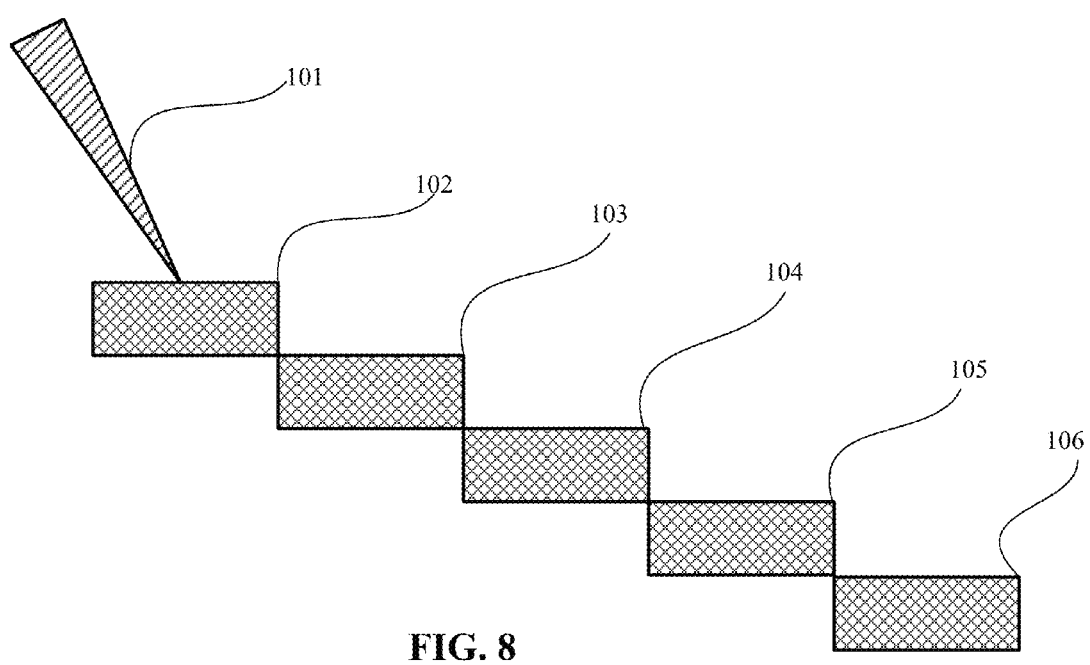
FIG. 8 shows 5 samples being picked up by the manipulator.

As shown in FIGS. 7 and 8, the process is repeated so that each subsequent lamella is attached to the preceding lamella that was attached. Lamella 105 is attached to lamella 104. Lamella 106 is attached to lamella 105. The attachment area can comprise a small section that allows for the electrostatic forces to make the attachment and also allows for the electrostatic forces to be greater than the weight of the total number of lamellas intended to be attached.

A computer, or processor, with the appropriate software, can receive the x-y coordinates for the multiple lamellas to be extracted from the FIB system. The location of each lamella can then be matched with a corresponding TEM sample holder location once the samples are extracted and transferred to the TEM sample holder, or TEM grid (typically one lamella per cell). This allows for data traceability through the entire process so that the final TEM results can be automatically matched back to the particular sample site on the original wafer.

Because electrostatic attraction is used to adhere the sample to the probe tip, the angled bevel on the microprobe, along with the ability to rotate the probe tip 180 degrees around its long axis, allows the lamella to be precisely placed on the TEM sample holder. Special consideration of the angle is also made when the sample is welded to the probe tip or to each other using FIB deposition.

Figure 9:
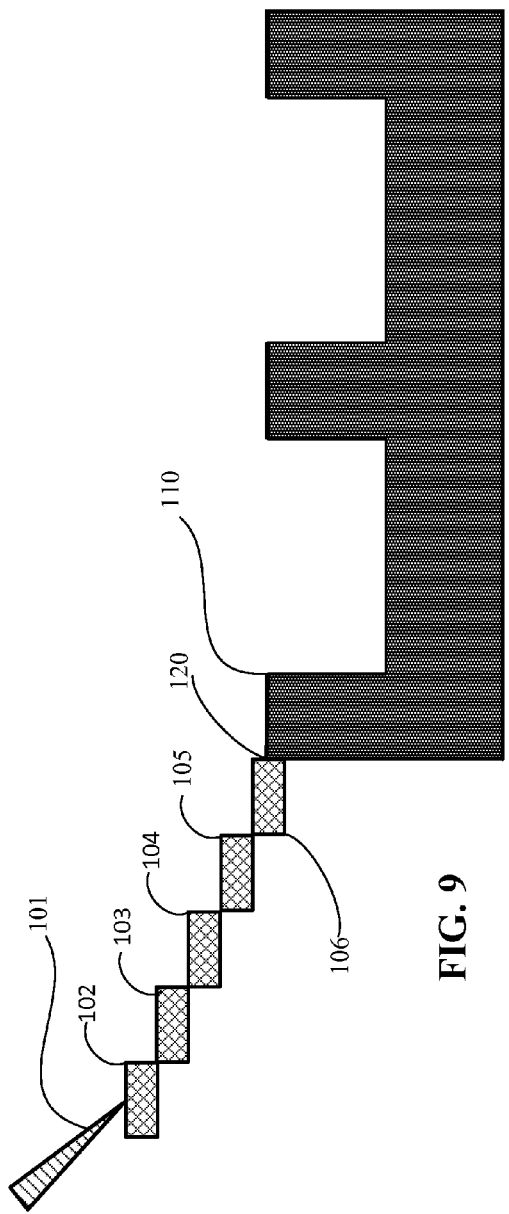
FIG. 9 shows 5 samples next to TEM sample holder.
Figure 10:
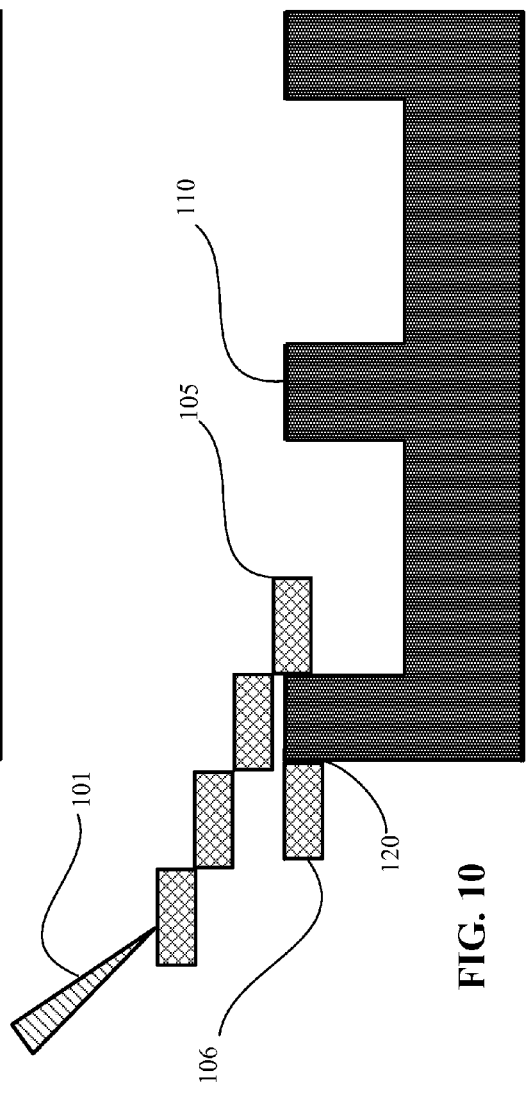
FIG. 10 shows the last sample (105) being welded to the holder (110).
Figure 11:
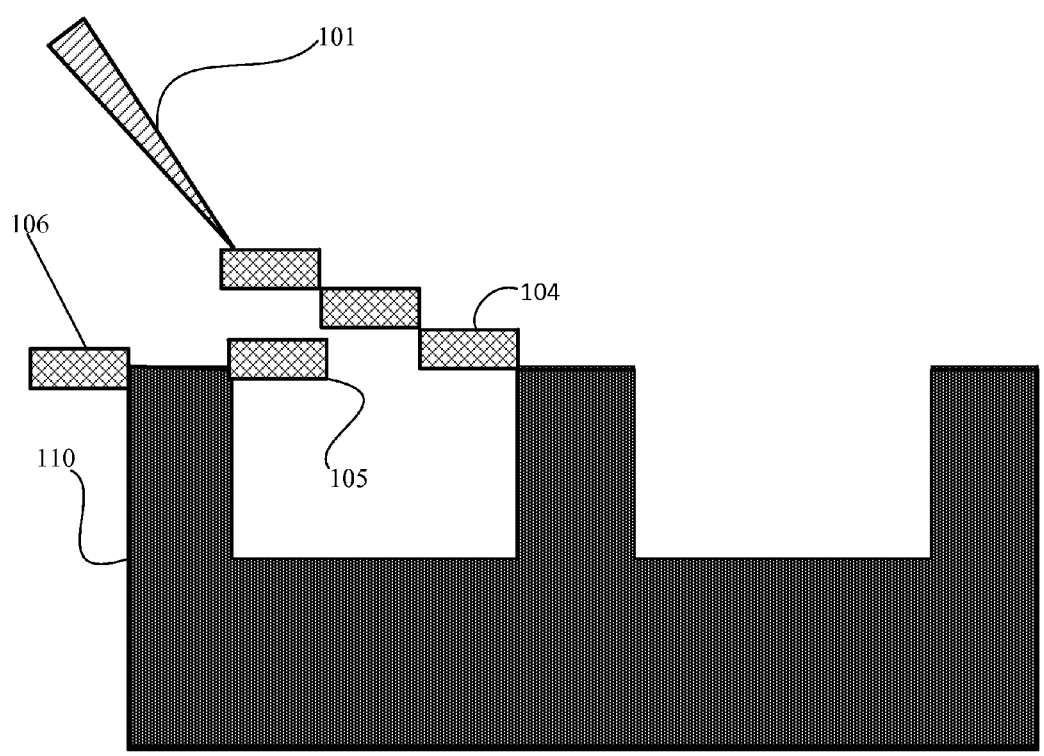
FIG. 11 shows sample (104) being attached to the grid.
Figure 12:
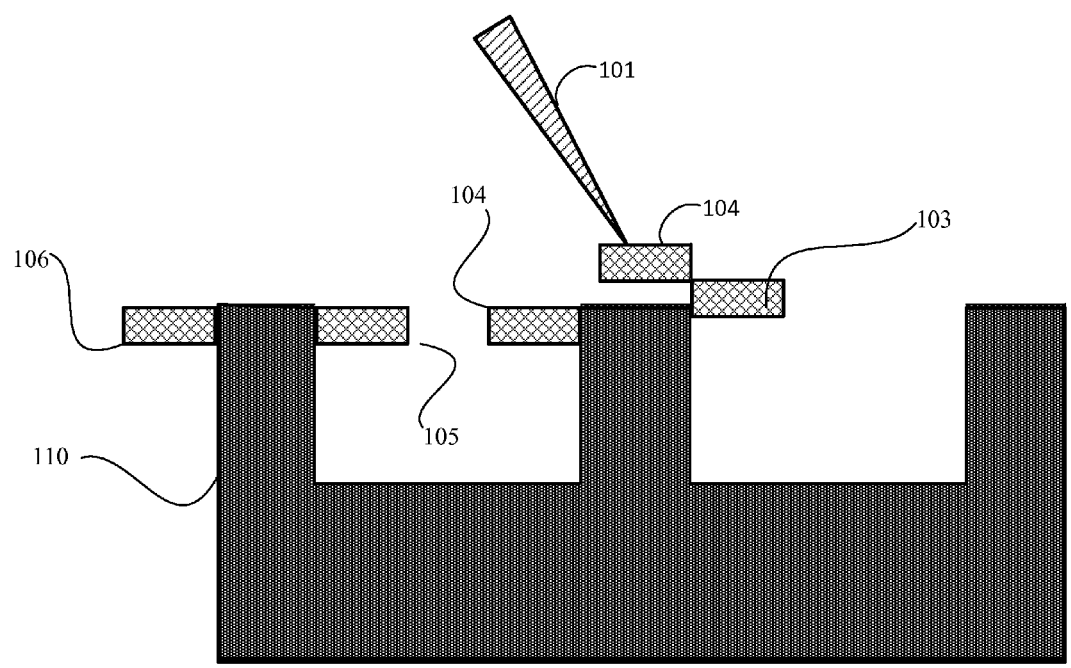
FIG. 12 shows sample (103) being attached to the grid.
Figure 13:
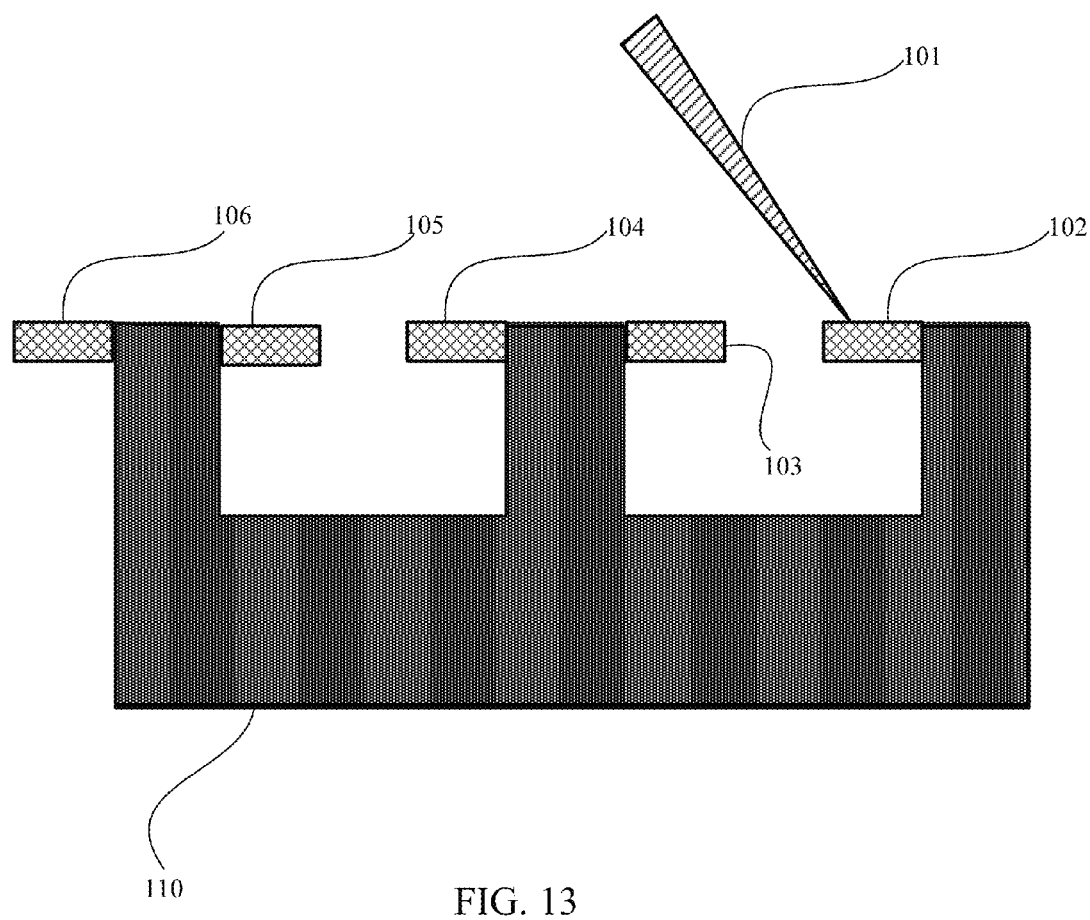
FIG. 13 shows sample (102) being attached to the grid.

Once all of the lamellas are picked up in a stacked formation, the lamellas are removed to a TEM sample holder, or a TEM grid, for placement. As shown in FIG. 9, the lamellas are dropped off onto TEM sample holder 110. The last lamella to be picked up, lamella 106 in FIG. 10, is lowered and positioned so that lamella 106 makes an attachment to TEM sample holder 110 at attachment spot 120. The electrostatic forces from the TEM sample holder 110 are stronger than the electrostatic forces that attach lamella 106 and lamella 105. Thus, the lamella 106 makes a willing attachment to TEM sample holder 110. In the alternative, the samples can be physically detached by severing the connection and making an attachment by welding the sample to the TEM sample holder 110. In accordance to FIGS. 11 through 13, the stacked lamellas are moved to a different location on the TEM sample holder 110 and removed one by one, wherein the last lamella extracted from the wafer is the first lamella to be lowered and attached to the TEM sample holder 110. This is done successively until all of the lamellas are removed from the micromanipulator 101 and attached to TEM sample holder 110.

The processing of the lamellas can be performed with an FIB system that can navigate to each additional sample site and repeat the process to prep each of the lamella. This may involve the process of milling each side of the desired sample locations. Because this method involves fewer motions between the bulk stage and the TEM sample holder, or TEM grid, the process minimizes stage motions, increases throughput, and minimizes the GIS insert/retract actions and manipulator insert retract actions. As automation of this process matures, a significant increase in throughput is expected.

Figure 14:
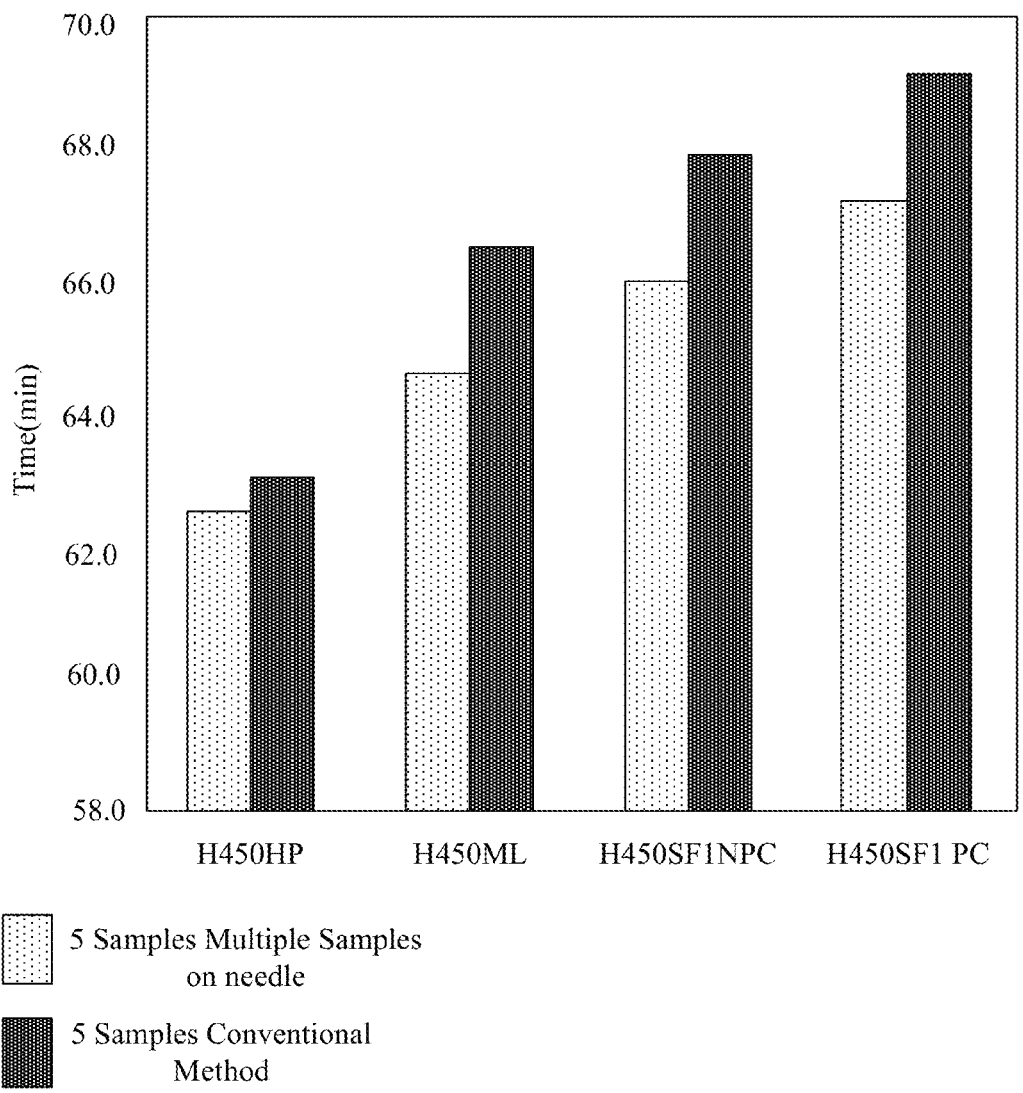
FIGS. 14 & 15 show graphs showing the average sample times for 5 samples using the conventional method and the methods in accordance with embodiments of the present invention.
Figure 15:
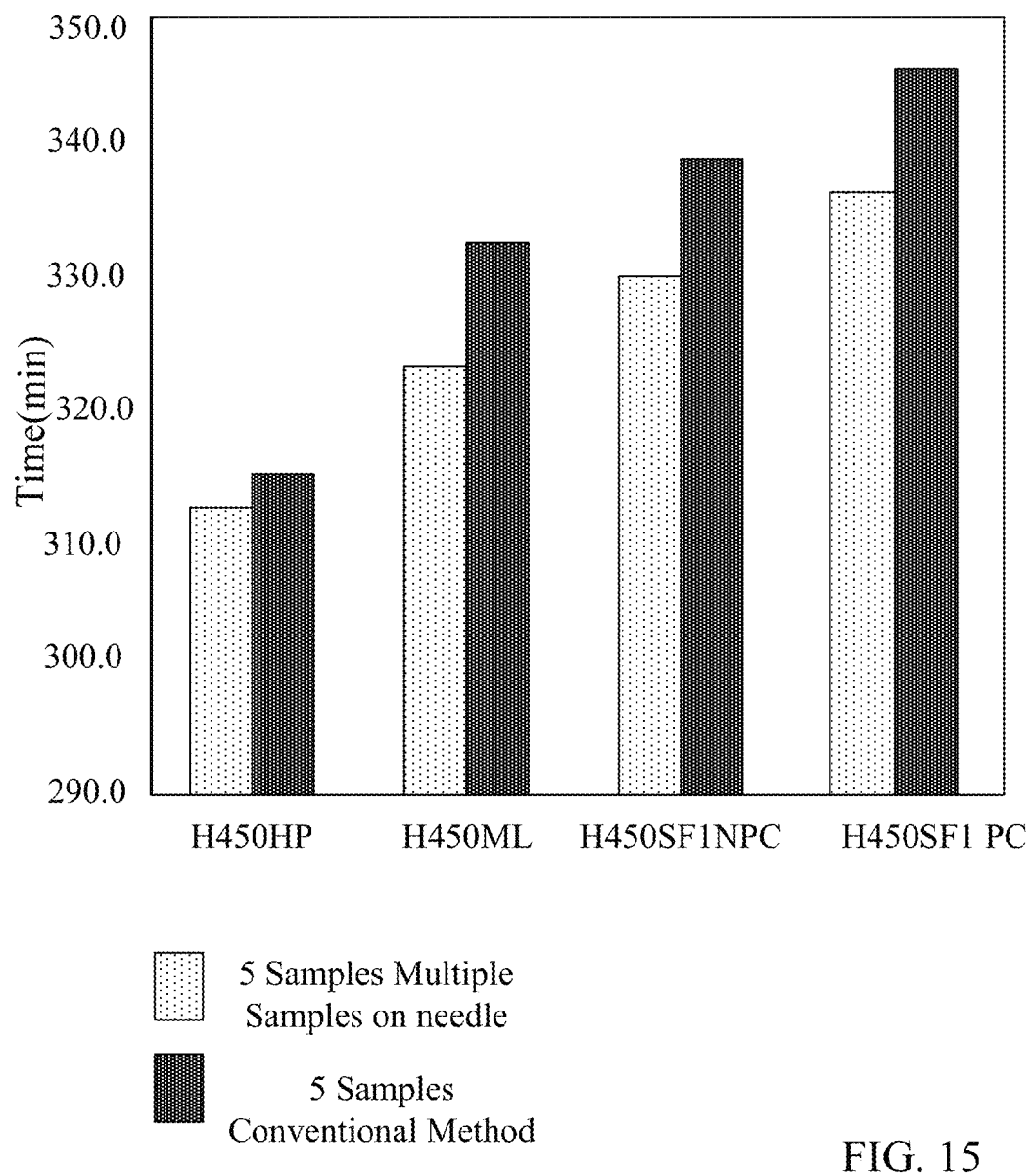

As shown in the FIGS. 14 and 15, which shows the average sample time for 5 samples using a H450HP, H450ML, H450SF1NPC, and H450SF1 PC using a conventional methods of extraction of lamellas and the method in accordance with embodiments of the current invention, almost 2 minutes per sample was reduced with the current method. The total sample time that is saved ranges from a couple of minutes to more than 10 minutes for given samples of 5 lamellas.

Figure 16:
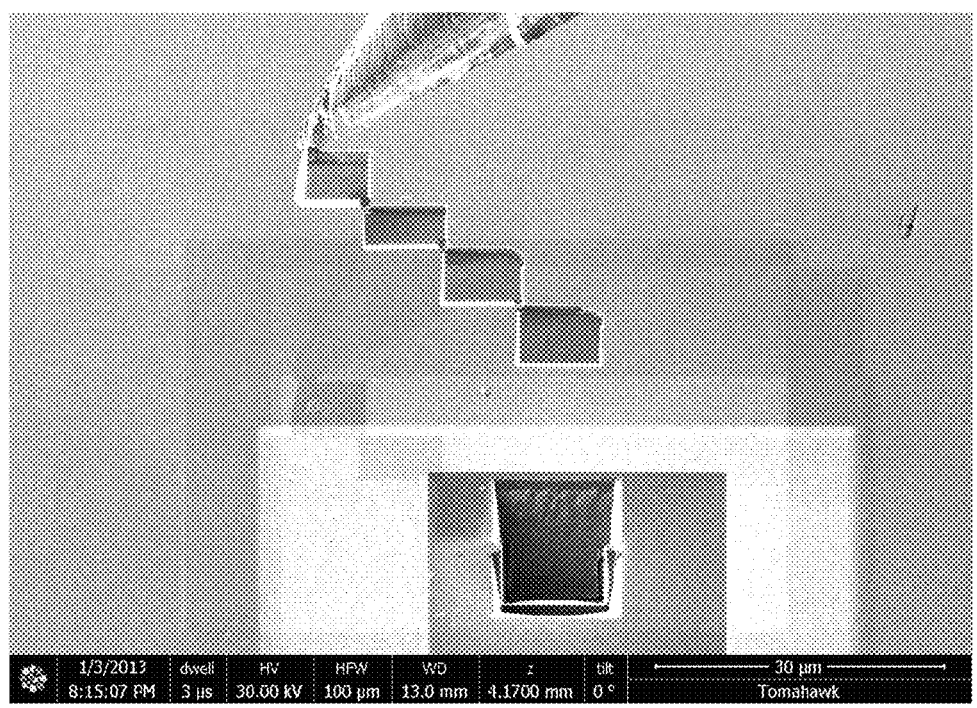
FIG. 16 is a picture of a microprobe holding multiple samples in accordance with embodiments of the present invention.
Figure 17:
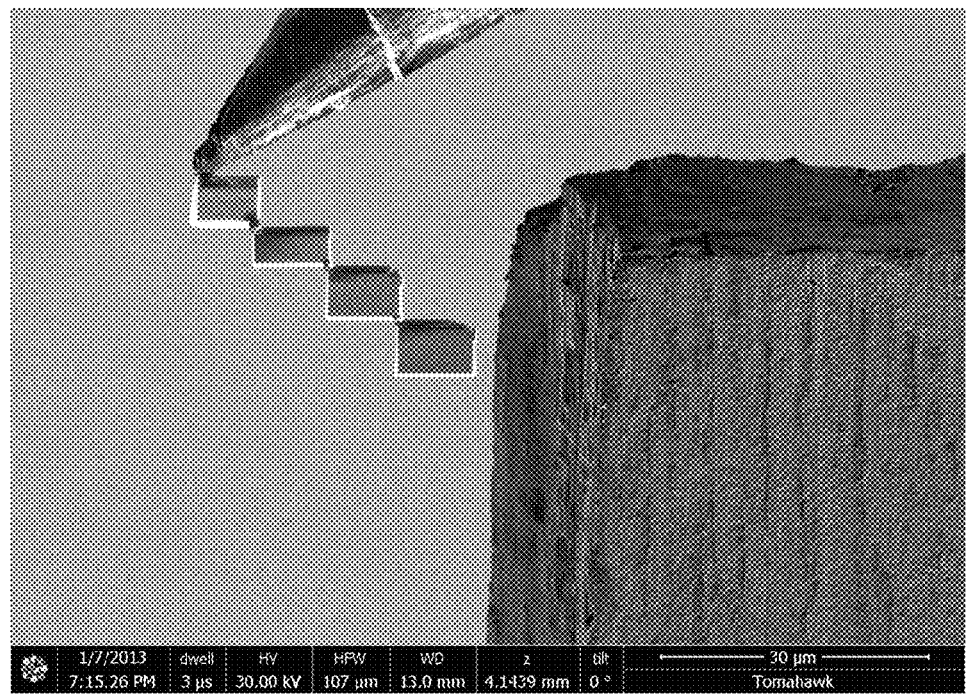
FIG. 17 shows a picture of a microprobe during a sample drop in accordance with embodiments of the present invention.

FIG. 16 shows a micromanipulator that has successfully picked up four lamellas in accordance with embodiments of the current invention. FIG. 17 shows an actual picture of a micromanipulator with the four lamellas that is intended for placement on the TEM sample holder.

The invention has broad applicability and can provide many benefits as described and shown in the examples above. The embodiments will vary greatly depending upon the specific application, and not every embodiment will provide all of the benefits and meet all of the objectives that are achievable by the invention. Further, although much of the previous description is directed at semiconductor wafers, the invention could be applied to any suitable substrate or surface. Also, although much of the previous description is directed at generally rectangular shaped lamellae which are less than 100 nm thick, the present invention could be used with lamellae of other thicknesses and with samples having other shapes. The accompanying drawings are intended to aid in understanding the present invention and, unless otherwise indicated, are not drawn to scale.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of extracting multiple lamella from a substrate comprising;
   preparing at least two lamella to be extracted;
   moving a manipulator into contact with a first lamella and attaching the first lamella to the manipulator;
   moving the manipulator so that the first lamella is in contact with a second lamella, which attaches the second lamella to the first lamella;
   extracting the first lamella and the second lamella with the manipulator.

2. The method of claim 1 wherein the attachment of the lamella to the manipulator is done with FIB deposition.

3. The method of claim 2 wherein the manipulator is a nano-manipulator.

4. The method of claim 1 wherein the attachment of the first lamella to the second lamella is done with FIB deposition.

5. The method of claim 1 wherein the steps further include:
   moving the manipulator with the attached first lamella and second lamella to a TEM sample holder so that the second lamella is in contact with a location on the TEM sample holder, wherein an electrostatic force attaches the second lamella to the location on the TEM sample holder and disconnects the second lamella from the first lamella;
   moving the manipulator with the attached first lamella to another location on the TEM sample holder and placing the first lamella in contact with a second location on the TEM sample holder so that the first lamella attaches to the second location on the TEM sample holder and disconnects from the manipulator.

6. The method of claim 1 wherein the steps further include:
   moving the manipulator with the attached first lamella and second lamella to a TEM sample holder so that the second lamella is in contact with a location on the TEM sample holder, wherein FIB deposition is used to weld the second lamella to the location on the TEM sample holder and disconnects the second lamella from the first lamella;
   moving the manipulator with the attached first lamella to another location on the TEM sample holder and placing the first lamella in contact with a second location on the TEM sample holder wherein FIB deposition is used to attach the first lamella to the second location on the TEM sample holder, which disconnects the first lamella from the manipulator.

7. The method of claim 6 wherein the second lamella is disconnected from the first lamella by a force of severing the connection when the second lamella is attached to the TEM sample holder.

8. The method of claim 6 wherein the TEM sample holder is a TEM grid.

9. The method of claim 1 wherein the steps further include:
   moving the manipulator to a third lamella and contacting the second lamella to the third lamella so that the second lamella attaches to the third lamella.

10. The method of claim 9 wherein the steps further include:
    moving the manipulator with the attached first lamella and second lamella and third lamella to a first location on a TEM sample holder so that the third lamella is in contact with the TEM sample holder at the first location,
    attaching the third lamella to the first location and detaching the third lamella from the second lamella,
    moving the manipulator with the attached first lamella and second lamella to a second location on the TEM sample holder and placing the second lamella in contact with the TEM sample holder at the second location;
    attaching the second lamella to the TEM sample holder at the second location and detaching the second lamella from the first lamella;
    moving the manipulator with the attached first lamella to a third location on the TEM sample holder and placing the first lamella in contact with the TEM sample holder at the third location;
    attaching the first lamella to the TEM sample holder at the third location.

11. The method of claim 10 wherein the TEM sample holder is a TEM grid.

12. A method of extracting multiple lamella from a substrate comprising;
    preparing multiple lamellas to be extracted;
    moving a nano-manipulator into contact with a first lamella and attaching the first lamella to the nano-manipulator;
    moving the nano-manipulator to each of the next multiple lamellas so that each subsequent lamellas is attached to the last lamella that was attached forming a stack of lamellas;
    moving the nano-manipulator with the stack of lamellas to a TEM sample holder;
    moving the nano-manipulator so that the last lamella on the stack of lamellas is in contact with a location on the TEM sample holder so that the last lamella is attached to the location;
    moving the nano-manipulator to other locations on the TEM sample holder and removing the lamella one by one in the reverse order that they were attached to the nano-manipulator.

13. The method of claim 12 wherein the TEM sample holder is a TEM grid.

14. The method of claim 12 wherein the attachment of the multiple lamellas are by electrostatic forces.

15. The method of claim 12 wherein the attachment of the multiple lamellas are by FIB deposition.

16. The method of claim 12 wherein the attachment of the lamella to the TEM sample holder is made by FIB deposition.

17. The method of claim 12 wherein the attachment of the lamella to the TEM sample holder results in a detachment of the lamella from the previous lamella by physically severing the connection.

* * * * *